(12) United States Patent
Enquist et al.

(10) Patent No.: US 9,285,251 B2
(45) Date of Patent: Mar. 15, 2016

(54) GAS SENSOR HOUSING

(75) Inventors: Fredrik Enquist, Linköping (SE); Peter Hebo, Mjölby (SE)

(73) Assignee: INFICON AB, Linkoping (SE)

( * ) Notice: Subject to any disclaimer, the term of this patent is extended or adjusted under 35 U.S.C. 154(b) by 145 days.

(21) Appl. No.: 13/817,497

(22) PCT Filed: Aug. 19, 2010

(86) PCT No.: PCT/SE2010/050898
§ 371 (c)(1),
(2), (4) Date: Feb. 18, 2013

(87) PCT Pub. No.: WO2012/023888
PCT Pub. Date: Feb. 23, 2012

(65) Prior Publication Data
US 2013/0145845 A1  Jun. 13, 2013

(51) Int. Cl.
G01D 11/24 (2006.01)
G01N 21/78 (2006.01)

(52) U.S. Cl.
CPC ............ G01D 11/245 (2013.01); G01N 21/783 (2013.01)

(58) Field of Classification Search
CPC ... G01D 11/245; G01N 21/783; G01N 27/12; G01N 27/407
USPC ...................... 73/31.04, 31.05, 431
See application file for complete search history.

(56) References Cited

U.S. PATENT DOCUMENTS

| | | | |
|---|---|---|---|
| 5,039,492 A | 8/1991 | Saaski et al. | |
| 5,055,270 A * | 10/1991 | Consadori et al. | 422/98 |
| 5,121,627 A | 6/1992 | D'Aoust | |
| 5,331,845 A * | 7/1994 | Bals et al. | 73/61.43 |
| 5,879,631 A * | 3/1999 | Wewers et al. | 422/98 |
| 6,868,350 B2 * | 3/2005 | Zimmermann et al. | 702/65 |
| 7,312,406 B2 * | 12/2007 | Oda | 174/521 |
| 7,479,255 B2 * | 1/2009 | Otani et al. | 422/94 |
| 7,827,851 B2 * | 11/2010 | Lee | 73/31.05 |
| 8,383,046 B1 * | 2/2013 | Tata | 422/82.05 |

(Continued)

FOREIGN PATENT DOCUMENTS

| | | |
|---|---|---|
| EP | 0 607 756 A2 | 7/1994 |
| GB | 983669 | 2/1965 |

(Continued)

OTHER PUBLICATIONS

International Preliminary Report on Patentability for PCT/SE2010/050898.

*Primary Examiner* — Peter Macchiarolo
*Assistant Examiner* — Natalie Huls
(74) *Attorney, Agent, or Firm* — Myers Bigel & Sibley, PA

(57) ABSTRACT

The present invention relates to gas sensor housing (1), comprising: a gas sensor (3) held by a housing body (11) below a primary gas permeable membrane (2); at least one connector element (10) molded into the housing body (11) such that the respective ends thereof enable connectivity to the gas sensor (3) such that signals may be carried from the gas sensor (3) to the connector element (10); a sensor envelope (9) providing an enclosure for the housing body (11); means for retaining the primary gas permeable membrane (2) in place above the gas sensor (3); a spacer section (7) providing a separation distance (X) between the gas sensor (3) and the primary gas permeable membrane (2).

19 Claims, 5 Drawing Sheets

(56) References Cited

U.S. PATENT DOCUMENTS

| | | | |
|---|---|---|---|
| 2002/0146352 A1* | 10/2002 | Wang et al. | 422/96 |
| 2004/0154379 A1* | 8/2004 | Enquist et al. | 73/40.7 |
| 2006/0179939 A1* | 8/2006 | Duval | 73/431 |
| 2008/0170600 A1* | 7/2008 | Sattler et al. | 374/163 |
| 2008/0190174 A1* | 8/2008 | Kooi et al. | 73/31.01 |
| 2009/0084160 A1* | 4/2009 | Bristol | 73/31.05 |
| 2009/0193872 A1* | 8/2009 | Tokuda et al. | 73/23.31 |
| 2011/0113860 A1* | 5/2011 | Nylander et al. | 73/31.07 |
| 2012/0018303 A1* | 1/2012 | Bordo et al. | 204/412 |
| 2012/0035850 A1* | 2/2012 | Risk et al. | 702/2 |
| 2014/0007649 A1* | 1/2014 | Niemann et al. | 73/23.2 |

FOREIGN PATENT DOCUMENTS

| | | |
|---|---|---|
| JP | H06242047 | 9/1994 |
| JP | 2007-003302 A | 1/2007 |
| JP | 2008300647 A | 12/2008 |
| JP | 2010-122100 A | 6/2010 |

\* cited by examiner

GAS SENSOR HOUSING

RELATED APPLICATIONS

The present application is a 35 U.S.C. §371 national phase application of PCT International Application No. PCT/SE2010/050898, having an international filing date of Aug. 19, 2010, the disclosure of which is hereby incorporated by reference herein in its entirety. The above PCT International Application was published in the English language as International Publication No. WO 2012/023888 A1.

The present invention relates to a gas sensor housing. In addition, the present invention relates to a test gas detection system comprising the gas sensor housing according to the invention and a leak testing system comprising the gas sensor housing according to the invention.

TECHNICAL FIELD

In leakage testing and leak detection using tracer gas, an object that is to be tested for leakage is filled with a gas or gas mixture, which contains at least one constituent detectable by means of a leakage detector. This leakage detector translates the presence of the traceable constituent, normally referred to as the tracer gas, into a digital, electrical, acoustic or optical signal.

Tracer gas is often used both to detect the presence and size of a leak and to locate a leak once detected. This is done by using the detector to register an increased content of the traceable substance in the vicinity of or in direct proximity to the leak.

For the detector to be able to register the leakage, at least a proportion of the tracer gas escaping must come into direct contact with the gas-sensitive sensor of the leakage detector. Currently two main principles are known for delivering the escaping tracer gas to the gas-sensitive sensor of the detector:
  a) A suction pipe with a nozzle (often referred to as a sniffer) is applied between the leakage site and the gas sensitive sensor. When the inlet orifice of the suction pipe is sufficiently close to the leakage site, tracer gas is sucked in from the leakage site and delivered through the suction pipe to close vicinity of the sensor sensitive to the tracer gas such that it may reach the sensor primarily by diffusion, whereupon the detector is arranged to emit a signal, e.g. optical and/or acoustic to alert an operator of a leakage.
  b) The gas-sensitive sensor is located so close to the leakage site that the tracer gas can reach the sensor sensitive to the tracer gas, primarily by diffusion, whereupon the detector is arranged to emit a signal, e.g. optical and/or acoustic to alert an operator of a leakage.

BACKGROUND OF THE INVENTION

Today sensor chips or beads are commonly mounted in standard housings, such as e.g. TO18, which is commonly used for housing transistors or other microelectronic devices. Another commonly used housing type is in the style first used by Figaro Engineering Inc. for its TGS 821—Special Sensor for Hydrogen Gas, which housing type is today used by many manufacturers of sensors.

Common for all sensor housings are that they are made to mechanically protect the sensing elements thereof against e.g. mechanical impact, dust and thermal shock.

In gas sensors gas may reach the sensor through directing a flow of sample gas onto an active surface of the sensing element. Although such a procedure ensures rapid establishment of the correct gas concentration on the active surface of the sensor, there is a significant risk that changes in flow or temperature may give rise to false readings.

Directing a gas flow onto the active surface also leads to an increased risk of particle contamination. It is therefore common that the sensing element is arranged to communicate with the ambient gas through diffusion only. A common way of doing this is to arrange a fine filter, such as a sintered disk or PTFE membrane in front of the sensing element. Such a fine filter is also commonly called diffusion membrane.

The diffusion principle is very robust but still suffers from a few drawbacks, such as slower establishment of the correct gas mixture on the active surface.

In one example application, manual leak detection, the sensor is often brought into close vicinity of the suspected leakage point or simply swept over a surface to be checked for leakage. It is evident that for such a use a high speed of response is beneficial.

When moving the sensor to a leak point there is also imminent risk of mechanical impact and contamination by dirt such as e.g. dust, oil and grease.

The housings of today commonly available sensors are typically not well suited to withstand such environments and leak detection probes are therefore normally fitted with at least one extra barrier in the probe tip for protecting the actual sensor housing. Such an extra protection barrier also adds to the delay in response of the detector.

Today commercially available sensors usually reside in housings which are typically equipped with a number of contact pins. A leak detection probe thus typically has a matching contact socket into which the contact pins of the sensor housing are inserted.

These today commercially available sensors are seldom suitable for application at the tip of a probe without any additional protection. Some sort of protective "cap" is therefore normally snapped or screwed on top of the sensor.

In addition to increasing the total distance, such a set up results in, at least, two filter barriers with a closed volume between them. The arrangement further reduces the diffusion speed by dividing the concentration gradient in two smaller gradients, each communicating with a volume closer to the active surface.

Usually, each of the individual filter barriers will need to be self supporting and therefore require a certain thickness. Thus, provision of one or more extra filter barriers usually renders an increase of thickness exceeding a mere aggregation of thicknesses.

SUMMARY OF THE INVENTION

Thus, it is an object of the invention to provide an improved gas sensor housing enabling an increased speed of reaction for detecting the presence of gas and a shorter recovery time for enabling subsequent detection.

This object is achieved by means of a gas sensor housing having the characteristics of claim 1.

The above objects are achieved thanks to the provision of a gas sensor housing, comprising: a gas sensor held by a housing body below a primary gas permeable membrane; at least one connector element moulded into the housing body such that the respective ends thereof enable connectivity to the gas sensor such that signals may be carried from the gas sensor to the connector element; a sensor envelope providing an enclosure for the housing body; means for retaining the primary gas permeable membrane in place above the gas sensor; a spacer section providing a separation distance between the gas sensor and the primary gas permeable membrane.

A further object of the present invention is to provide an improved test gas detection system.

This further object is achieved by means of a test gas detection system having the characteristics of claim 14.

A still further object of the present invention is to provide an improved leak testing system.

This still further object is achieved by means of a test gas detection system having the characteristics of claim 15.

Preferred embodiments are listed in the dependent claims.

BRIEF DESCRIPTION OF THE DRAWINGS

By way of example only, embodiments of the present invention will now be described with reference to the accompanying drawings wherein.

Figure 1:
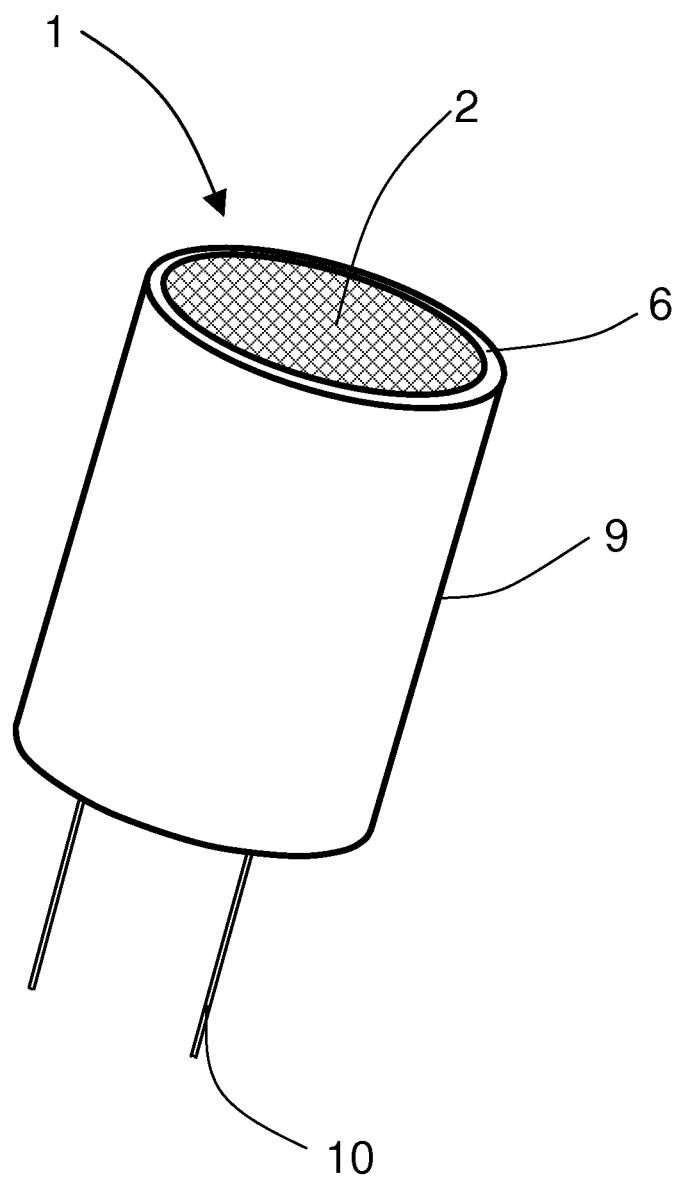
FIG. 1 is an exterior view of a gas sensor housing in accordance with the present invention.

Still other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein. The same reference numerals will be used for illustrating corresponding features in the different drawings.

DETAILED DESCRIPTION OF PREFERRED EMBODIMENTS

The present invention is based on that in accordance with Fick's second law of diffusion, the time needed to establish a certain concentration on an active surface of a gas sensor is proportional to the square of the distance between the active surface and an external surface of a diffusion membrane.

$$\frac{\partial \phi}{\partial t} = D \frac{\partial^2 \phi}{\partial x^2}$$

Where
$\phi$ is the concentration in mol/m$^3$
t is the time in s
D is the diffusion coefficient in m$^2$/s
x is the diffusion distance in m Fick's first law shows that the gas flow through the diffusion membrane is proportional to the concentration gradient across the membrane.

$$J = -D \frac{\partial \phi}{\partial x}$$

Where
J is the flow in mol/(m$^2$s)

These two basic properties of diffusion have been found to slow down the response time and recovery time of the today known sensors. The recovery time of the today known sensors lies in the size order of 60-70 seconds. Note that although some detectors today state recovery times of 1-10 seconds, this is an instrument level and usually correspond to t90%. The instruments accelerate the reset such that they will display zero a substantial time before the actual sensor has recovered.

It has thus been realized that in accordance with Fick's laws it should be advantageous to minimize the diffusion distance and the internal volume behind the diffusion membrane.

Thus, when integrating a gas sensor in a manual or other probe requiring an extra protection barrier it is desirable to minimize the distance that the gas to be detected will have to diffuse to reach the active surface.

In FIG. 1 is shown an exterior view of a gas sensor housing 1 in accordance with the present invention. The gas sensor housing 1 has a primary gas permeable membrane 2, or diffusion membrane 2, through which gas to be detected will need to diffuse. This primary gas permeable membrane 2 may e.g. as shown be held in place by an inwardly protruding edge 6 of a sensor envelope 9, which e.g. may be a metal envelope. Alternatively the primary gas permeable membrane 2 may be held in place through gluing or welding. A pair of connector elements 10 protrudes from the bottom of the gas sensor housing 1.

Figure 2:
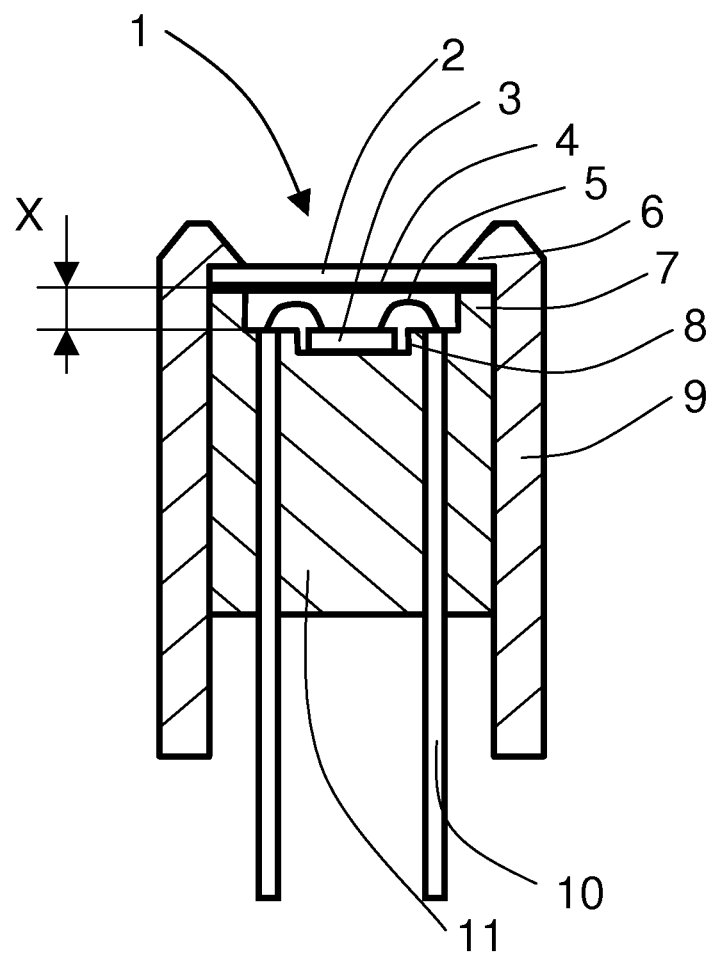
FIG. 2 is a section through one embodiment of a gas sensor housing according to FIG. 1.

FIG. 2 illustrates a section through a first embodiment of a gas sensor housing according to FIG. 1. A gas sensor 3 is held by a housing body 11 below the primary gas permeable membrane 2. The housing body 11 may be moulded from thermoplastic material, such as a thermoplastic material at least partially comprising Polyether Ether Ketone (PEEK), in order to provide for a low cost of production. PEEK has excellent thermal and mechanical properties for temperatures up to about 250° C.

Two connector elements 10 are moulded into the housing body 11 such that the respective ends thereof protrude from the bottom of the housing body 11 and such that they reach the top of the housing body 11, enabling connectivity to the gas sensor 3. Connector leads 5 connect the connector elements 10 with the gas sensor 3, such that electrical signals may be carried from the gas sensor 3 to the connector elements 10. The connector leads 5 may be precious metal alloy wire leads 5 and may further be welded to the connector elements 10.

The sensor envelope 9 provides an enclosure for the housing body 11 and retains the primary gas permeable membrane 2 in place above the gas sensor 3 through the inwardly protruding edge 6. The inwardly protruding edge 6 of the sensor envelope 9 thus restricts movement of the primary gas permeable membrane 2 away from the housing body 11. An annular spacer section 7 integrally formed with the housing body 11 and at least partially encircling the gas sensor 3 provides for a separation distance X between the gas sensor 3 and the primary gas permeable membrane 2, which separation distance X also provides the necessary space for accommodating the connector leads 5. As mentioned above, in alternative embodiments, the primary gas permeable membrane 2 may be held in place through being glued or welded to either one of or to both of the sensor envelope 9 and the annular spacer section 7.

As shown in FIG. 2, the gas sensor 3 may rest in a recessed section 8 of the housing body 11. In an alternative embodiment the gas sensor 3 may of course rest on a non-recessed planar surface of the housing body 11, even if such an arrangement would be less advantageous as the volume of the space created between the housing body 11 and the primary gas permeable membrane 2 would be larger than in the embodiment shown in FIG. 2.

In a yet further embodiment it is envisaged to minimize the volume of the space created between the housing body 11 and the primary gas permeable membrane 2, i.e. the separation distance X between the gas sensor 3 and the primary gas permeable membrane 2, even further. This is possible by introducing an optional secondary gas permeable membrane 4 between the annular spacer section 7 of the housing body 11 and the primary gas permeable membrane 2. Through applying a secondary gas permeable membrane 4 which has electrically insulating properties it is possible to reduce the separation distance X even further, as the secondary gas permeable membrane 4 would then ensure that the connector leads 5 do not contact the possibly electrically conductive primary gas permeable membrane 2.

Such a secondary gas permeable membrane 4 may e.g. be made at least partially from Polytetrafluoroethylene (PTFE) or similar halogenated hydrocarbon polymer. Suitable membranes are e.g. provided by Millipore Corporation. Such PTFE membranes provide excellent electrical insulation properties, and have excellent thermal and mechanical properties for temperatures up to about 250° C.

In an embodiment where a secondary diffusion membrane 4 is applied it is possible to exchange the primary diffusion membrane 2 with a more open structure, such as a metal mesh. In this case the metal mesh only serves the purpose of retaining and mechanically protecting the second diffusion membrane 4. This is advantageous as a metal mesh often may be made thinner than the commonly used sintered discs.

Figure 3:
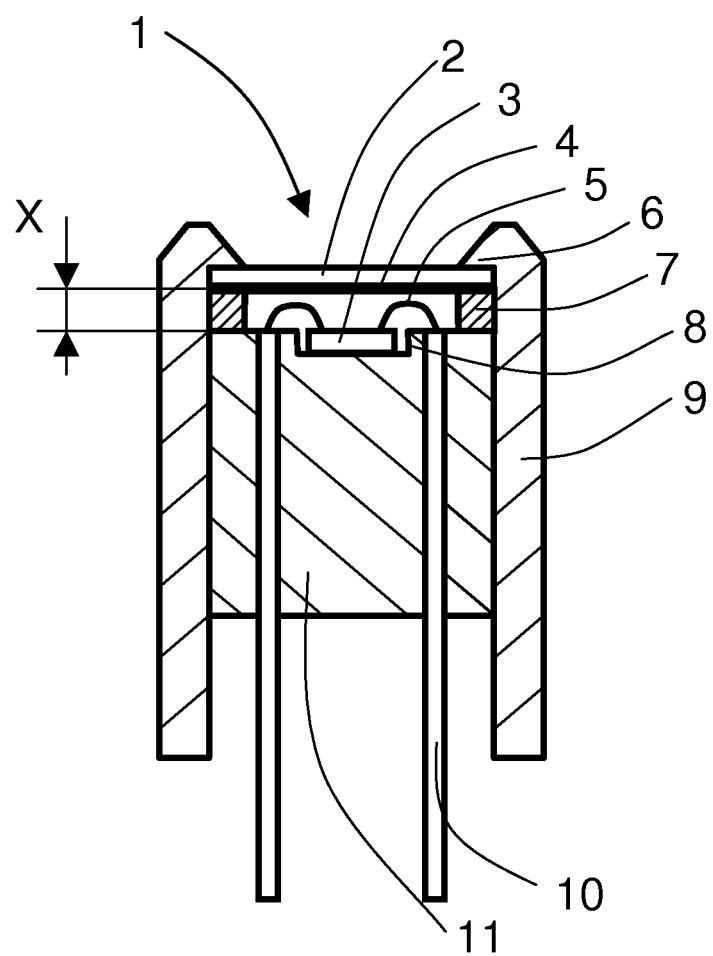
FIG. 3 is a section through an alternative embodiment of a gas sensor housing according to FIG. 1.

An alternative embodiment of a gas sensor housing 1 in accordance with the present invention is shown in FIG. 3, which illustrates a section through this alternative embodiment of the gas sensor housing according to FIG. 1. As in the first embodiment, a gas sensor 3 is held by a housing body 11 below a primary gas permeable membrane 2.

The two connector elements 10 are as in the first embodiment moulded into the housing body 11 such that the respective ends thereof protrude from the bottom of the housing body 11 and such that they reach the top of the housing body 11, enabling connectivity to the gas sensor 3. The connector leads 5, as in the first embodiment, connect the connector elements 10 with the gas sensor 3, such that electrical signals may be carried from the gas sensor 3 to the connector elements 10.

As in the first embodiment, the sensor envelope 9 provides an enclosure for the housing body 11 and retains the primary gas permeable membrane 2 in place above the gas sensor 3 through the inwardly protruding edge 6. The inwardly protruding edge 6 of the sensor envelope 9 thus restricts movement of the primary gas permeable membrane 2 away from the housing body 11. Alternatively, as described earlier, the primary gas permeable membrane 2 may be held in place through gluing or welding.

Figure 4:
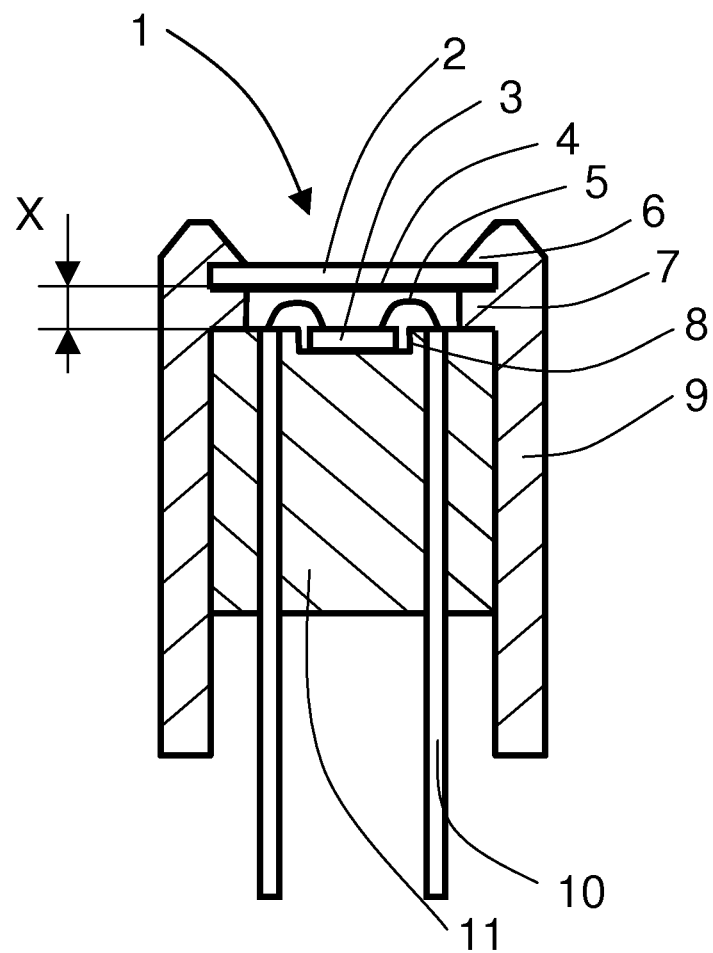
FIG. 4 is a section through yet an alternative embodiment of a gas sensor housing according to FIG. 1.

However, differentiating this alternative embodiment according to FIG. 3 from the embodiment of FIG. 1, is the fact that the annular spacer section 7, which at least partially encircles the gas sensor 3 and provide for the separation distance X between the gas sensor 3 and the primary gas permeable membrane 2, in this alternative embodiment according to FIG. 3 is not integrally formed with the housing body 11 but rather a separate entity arranged between the housing body 11 and the primary gas permeable membrane 2. A yet further alternative embodiment is shown in FIG. 4. The embodiment according to FIG. 4 differs from the embodiments according to FIGS. 2 and 3 in that the spacer section 7, which at least partially encircles the gas sensor 3 and provide for the separation distance X between the gas sensor 3 and the primary gas permeable membrane 2, in this yet further alternative embodiment according to FIG. 4 is integrally formed with the sensor envelope 9. In still alternative embodiments, the primary gas permeable membrane 2 may, as indicated above, be held in place through being glued or welded to either one of or to both of the sensor envelope 9 and the annular spacer section 7.

As shown in FIG. 3, the gas sensor 3 may, as in the first embodiment, rest in a recessed section 8 of the housing body 11, or in a further alternative embodiment the gas sensor 3 may of course rest on a non-recessed planar surface of the housing body 11, even if such an arrangement would be less advantageous as the volume of the space created between the housing body 11 and the primary gas permeable membrane 2 would be larger than in the embodiment shown in FIG. 3.

In a still further alternative embodiment it is envisaged to minimize the volume of the space created between the housing body 11 and the primary gas permeable membrane 2, i.e. the separation distance X between the gas sensor 3 and the primary gas permeable membrane 2, even further. This is, as in the first embodiment, possible by introducing an optional secondary gas permeable membrane 4 between the annular spacer section 7 and the primary gas permeable membrane 2. Through applying a secondary gas permeable membrane 4 which has electrically insulating properties it is possible to reduce the separation distance X even further, as the secondary gas permeable membrane 4 would then ensure that the connector leads 5 do not contact the possibly electrically conductive primary gas permeable membrane 2.

For an optimal performance it is preferable to use the above proposed gas sensor housings 1 of the different proposed embodiments with gas sensors 3 being planar chip gas sensors 3. Thin film gas sensors 3 have been found to provide excellent performance through providing for more rapid diffusion and recovery as compared to other types of sensors. The recovery time for thin film gas sensors 3 lies in the size order of 10 seconds, as compared to today commonly used sensors the recovery times of which usually lie in the size order of 60-70 seconds.

Figure 5:
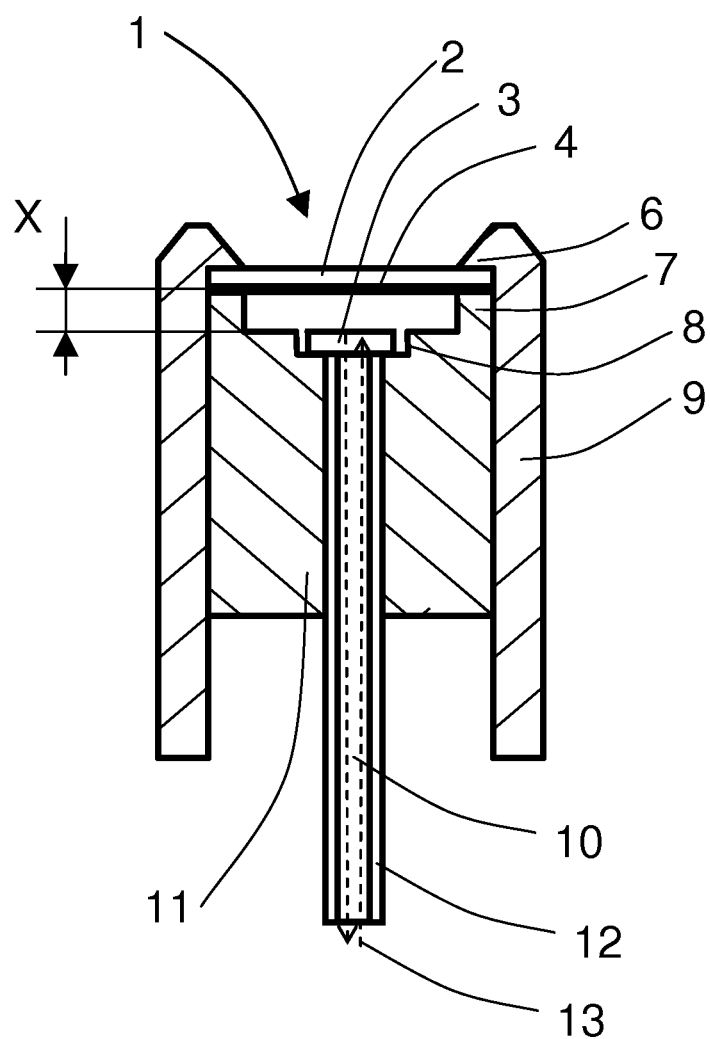
FIG. 5 is a section through still an alternative embodiment of a gas sensor housing according to FIG. 1, comprising an optical sensor.

In a still further alternative embodiment according to FIG. 5 is shown a section through a gas sensor housing according to FIG. 1. However, in this embodiment an optical gas sensor 3 is held by the housing body 11 below the primary gas permeable membrane 2. The housing body 11 may, as before, be moulded from thermoplastic material, such as a thermoplastic material at least partially comprising Polyether Ether Ketone (PEEK).

A connector element 10 is provided by a fiber optic conductor with a cladding 12, which connector elements 10 is moulded into the housing body 11 such that an end thereof is accessible near the bottom of the housing body 11 and such it reaches the gas sensor 3, such that optical signals (dotted arrows 13) may be carried to and from the gas sensor 3.

The sensor envelope 9 provides an enclosure for the housing body 11 and retains the primary gas permeable membrane 2 in place above the gas sensor 3 through the inwardly protruding edge 6. The inwardly protruding edge 6 of the sensor envelope 9 thus restricts movement of the primary gas permeable membrane 2 away from the housing body 11. Alternatively, as described earlier, the primary gas permeable membrane 2 may be held in place through gluing or welding. An annular spacer section 7 integrally formed with the housing body 11 and at least partially encircling the gas sensor 3 provides for a separation distance X between the gas sensor 3 and the primary gas permeable membrane 2. Alternatively, the separation distance X may of course be provided in accordance with the FIG. 3 or FIG. 4 embodiments. In yet further alternative embodiments, the primary gas permeable membrane 2 may, as indicated above, be held in place through being glued or welded to either one of or to both of the sensor envelope 9 and the annular spacer section 7.

As an example, an optical gas sensor sensitive to hydrogen ($H_2$) may be achieved through coating a Bragg-filter/screen or a mirror with Palladium (Pd) whereby a change in optical properties (diffraction) will occur as gas is absorbed. Other examples include materials that change color when exposed to a certain or certain gases, and thereby the reflection and/or absorption of light of a certain wavelength.

The present invention further relates to a test gas detection system comprising a gas sensor housing 1 according to any one of the above described embodiments.

The present invention further relates to a leak testing system comprising a gas sensor housing 1 according to any one of the above described embodiments.

Such test gas detection systems and leak testing systems typically comprises a gas sensor contained in a housing, an optical or electric conductor carrying signals from the sensor to evaluation circuitry, an instrument comprising: the evaluation circuitry; human-machine interfaces and machine-machine interfaces. In the case where the system is intended for manual operation it is also common that the system comprises a handle on which the sensor and sometimes also the evaluation circuitry or even the complete instrument is mounted.

Modifications to embodiments of the invention described in the foregoing are possible without departing from the scope of the invention as defined by the accompanying claims.

Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural and vice versa.

Numerals included within parentheses in the accompanying claims are intended to assist understanding of the claims and should not be construed in any way to limit subject matter claimed by these claims.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas sensor housing, comprising:
   a gas sensor, for establishment of a gas concentration on an active surface of the gas sensor, held by a housing body below a primary gas permeable diffusion membrane through which gas to be detected by the gas sensor will need to diffuse in accordance with Fick's second law of diffusion;
   at least one connector element moulded into the housing body such that the respective ends thereof enable connectivity to the gas sensor such that signals may be carried from the gas sensor to the connector element;
   a sensor envelope providing an enclosure for the housing body;
   a spacer section providing the necessary space for accommodating at least one connector lead connecting the at least one connector element with the gas sensor and thus a separation distance between the gas sensor and the primary gas permeable diffusion membrane providing a minimized volume space between the housing body and the primary gas permeable diffusion membrane and a minimized distance that the gas to be detected will have to diffuse to reach the active surface of the gas sensor;
   an inwardly protruding edge of the sensor envelope retaining the primary gas permeable membrane in place above the gas sensor and restricting movement of the primary gas permeable membrane away from the housing body;
   a secondary gas permeable diffusion membrane having electrically insulating properties ensuring that the at least one connector lead does not connect electrically to the primary gas permeable diffusion membrane between the spacer section and the primary gas permeable membrane.

2. A gas sensor housing according to claim 1, wherein the spacer section is integrally formed with the housing body.

3. A gas sensor housing according to claim 1, wherein the spacer section is a separate entity arranged between the housing body and the primary gas permeable membrane.

4. A gas sensor housing according to claim 1, wherein the spacer section is integrally formed with the sensor envelope.

5. A gas sensor housing according to claim 1, wherein the secondary gas permeable membrane is made at least partially from Polytetrafluoroethylene or similar halogenated hydrocarbon polymer.

6. A gas sensor housing according to claim 1, wherein the housing body is moulded from thermoplastic material.

7. A gas sensor housing according to claim 6, wherein the housing body is moulded from a thermoplastic material at least partially comprising Polyether Ether Ketone.

8. A gas sensor housing according to claim 1, wherein the gas sensor is a planar chip gas sensor.

9. A gas sensor housing according to claim 1, wherein the gas sensor is a thin film gas sensor.

10. A test gas detection system comprising a gas sensor housing according to claim 1.

11. A gas sensor housing according to claim 1, further comprising the at least one connector lead in the minimized volume space between the housing body and the primary gas permeable diffusion membrane, the at least one connector lead electrically connecting the at least one connector element with the gas sensor.

12. A gas sensor housing according to claim 11, wherein the at least one connector element comprises a plurality of connector elements and the at least one connector lead comprises a plurality of connector leads.

13. A gas sensor housing according to claim 11, wherein the at least one connector lead is adjacent the secondary gas permeable diffusion membrane.

14. A gas sensor housing according to claim 1, wherein the gas sensor is in a recessed section of the housing body.

15. A gas sensor housing according to claim 1, wherein the primary gas permeable diffusion membrane and the secondary gas permeable diffusion membrane are held between the spacer section and the inwardly protruding edge of the sensor envelope.

16. A gas sensor housing according to claim 1, wherein the secondary gas permeable diffusion membrane is directly between the primary gas permeable diffusion membrane and the spacer section.

17. A gas sensor housing, comprising:
a gas sensor, for establishment of a gas concentration on an active surface of the gas sensor, held by a housing body below a primary gas permeable diffusion membrane through which gas to be detected by the gas sensor will need to diffuse in accordance with Fick's second law of diffusion;
at least one connector element moulded into the housing body such that the respective ends thereof enable connectivity to the gas sensor such that signals may be carried from the gas sensor to the connector element;
a sensor envelope providing an enclosure for the housing body;
a spacer section providing the necessary space for accommodating at least one connector lead connecting the at least one connector element with the gas sensor and thus a separation distance between the gas sensor and the primary gas permeable diffusion membrane providing a minimized volume space between the housing body and the primary gas permeable diffusion membrane and a minimized distance that the gas to be detected will have to diffuse to reach the active surface of the gas sensor;
the primary gas permeable diffusion membrane being held in place above the gas sensor through being glued or welded to either one of or to both of the sensor envelope and the spacer section;
a secondary gas permeable diffusion membrane having electrically insulating properties ensuring that the at least one connector lead does not connect electrically to the primary gas permeable diffusion membrane between the spacer section and the primary gas permeable membrane.

18. A gas sensor housing according to claim 1, wherein the minimized volume space is a closed space communicating to the surrounding only via the primary gas permeable diffusion membrane and the secondary gas permeable diffusion membrane.

19. A gas sensor housing, comprising:
a gas sensor, for establishment of a gas concentration on an active surface of the gas sensor, held by a housing body below a metal mesh or sintered disc;
at least one connector element moulded into the housing body such that the respective ends thereof enable connectivity to the gas sensor such that signals may be carried from the gas sensor to the connector element;
a sensor envelope providing an enclosure for the housing body;
a spacer section providing the necessary space for accommodating at least one connector lead connecting the at least one connector element with the gas sensor and thus a separation distance between the gas sensor and the metal mesh or sintered disc providing a minimized volume space between the housing body and the metal mesh or sintered disc and a minimized distance that the gas to be detected will have to diffuse to reach the active surface of the gas sensor;
an inwardly protruding edge of the sensor envelope retaining the metal mesh or sintered disc in place above the gas sensor and restricting movement of the metal mesh or sintered disc away from the housing body;
a secondary gas permeable diffusion membrane having electrically insulating properties ensuring that the at least one connector lead does not connect electrically to the metal mesh or sintered disc between the spacer section and the metal mesh or sintered disc through which secondary gas permeable diffusion membrane gas to be detected by the gas sensor will need to diffuse in accordance with Fick's second law of diffusion.

* * * * *